(12) United States Patent
Wehrli

(10) Patent No.: US 9,561,993 B2
(45) Date of Patent: Feb. 7, 2017

(54) PROCESS FOR THE MANUFACTURE OF DIBENZOYLMETHANE DERIVATIVES

(75) Inventor: Christof Wehrli, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 594 days.

(21) Appl. No.: 13/996,042

(22) PCT Filed: Dec. 19, 2011

(86) PCT No.: PCT/EP2011/073172
§ 371 (c)(1),
(2), (4) Date: Sep. 3, 2013

(87) PCT Pub. No.: WO2012/084770
PCT Pub. Date: Jun. 28, 2012

(65) Prior Publication Data
US 2014/0017183 A1    Jan. 16, 2014

(30) Foreign Application Priority Data
Dec. 20, 2010    (EP) .................................... 10195971

(51) Int. Cl.
*C07C 45/45* (2006.01)
*C07C 49/84* (2006.01)

(52) U.S. Cl.
CPC ............. *C07C 45/45* (2013.01); *C07C 45/455* (2013.01); *C07C 49/84* (2013.01)

(58) Field of Classification Search
CPC .................................................. C07C 45/45
See application file for complete search history.

(56) References Cited

U.S. PATENT DOCUMENTS

| | | | |
|---|---|---|---|
| 4,387,089 | A | 6/1983 | DePolo |
| 5,344,992 | A | 9/1994 | Drewes et al. |
| 6,278,025 | B1 | 8/2001 | Habeck et al. |
| 6,410,795 | B1 | 6/2002 | Fisch et al. |
| 2009/0246156 | A1 | 10/2009 | Kunin |

FOREIGN PATENT DOCUMENTS

| | | |
|---|---|---|
| DE | 29 45 125 | 5/1980 |
| DE | 44 27 512 | 2/1996 |
| JP | 55-66535 | 5/1980 |

OTHER PUBLICATIONS

International Search Report for PCT/EP2011/073172, mailed Apr. 24, 2012.
Nandurkar et al., "Synthesis of sterically hindered 1,3-dieketones", *Synthetic Communications*, vol. 37, No. 23, Jan. 1, 2007, pp. 4111-4115.
Guoqing et al., "Polymorphism and Reversible Mechanochromic Luminescence for Solid-State Difluoroboron Avobenzone", *Journal of the American Chemical Society*, vol. 132, Jan. 1, 2010, pp. 2160-2162.
Franek, "New Dithio-bis-(diaroylmethanes) and Acetyl Diaroylchloromethyl Disulfides: Attractive Synthons and Precursors for the Liberation of Highly Reactive Dithiiranes or Thiosulfines", *Monatshefte Fur Chemie*, vol. 127, Jan. 1, 1996, pp. 895-907.
Ishida et al., "Antitumor Agents. Part 214: Synthesis and Evaluation of Curcumin Analogues as Cytotoxic Agents", *Bioorganic & Medicinal Chemistry Pergamon*, GB, vol. 10, Jan. 1, 2002, pp. 3481-3487.

*Primary Examiner* — Benjamin Packard
(74) *Attorney, Agent, or Firm* — Nixon & Vanderhye P.C.

(57) ABSTRACT

The invention relates to a process for the manufacture of substituted dibenzoylmethane derivatives. This economical process provides products in high purity and yields and results in shorter reaction times.

19 Claims, No Drawings

PROCESS FOR THE MANUFACTURE OF DIBENZOYLMETHANE DERIVATIVES

This application is the U.S. national phase of International Application No. PCT/EP2011/073172 filed 19 Dec. 2011 which designated the U.S. and claims priority to EP Patent Application No. 10195971.6 filed 20 Dec. 2010, the entire contents of each of which are hereby incorporated by reference.

The invention relates to an improved process for the manufacture of substituted dibenzoylmethane derivatives. This novel economical process provides products in high purity and yields and results in shorter reaction times.

Substituted dibenzoylmethane derivatives are highly effective UVA-absorbers which are, for example, used as light stabilizers in plastics or as light screening agents in cosmetic products. Customary dibenzoylmethane derivatives are, for example, Eusolex® 8020 [INCI Name: Isopropyldibenzoylmethane; CAS No.: 63250-25-9] or PARSOL® 1789 [INCI Name: butyl methoxydibenzoylmethane; 4-tert-butyl-4'-methoxydibenzoylmethane, CAS No.: 70356-09-1].

Substituted dibenzoylmethane derivatives may be prepared by Aldol condensation of a ketone with an ester in the presence of a strong base such as e.g. disclosed in DE 2945125 or U.S. Pat. No. 6,278,025. Suitable bases cited by the references are sodium hydride, sodium amide or alkali or earth alkali metal alkoxides such as in particular sodium methylate.

Because of the continuously increasing demand for dibenzoylmethane based light screening agents the object of the present invention was to provide a process for the preparation of substituted dibenzoylmethane derivatives which is easy to carry out and affords economic advantages as a result of high yields. Furthermore, the process yields purer products as the hardly removable symmetric by-products are formed to a lesser extend. This is particularly important because minor impurities tend to impart a color to the product which is unwanted for use in cosmetic formulations.

Surprisingly, it has been found that the use of potassium alcoholate as base delivers higher yields and less side products compared to the use of other bases. Furthermore, the intermediate potassium salt formed during the reaction does not crystallize in the reaction mixture, thus facilitating industrial handling. Additionally, the reaction times can be reduced by the use of a potassium alcoholate as base.

Thus, the invention relates to a process for the preparation of substituted dibenzoylmethane derivatives of formula (I)

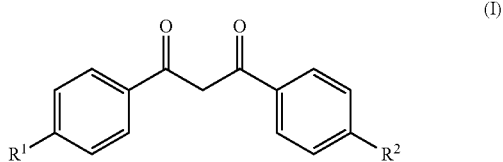

(I)

wherein
$R^1$ and $R^2$ are independently selected from the group consisting of hydrogen, $C_1$ to $C_{12}$ alkyl, $C_1$ to $C_{12}$ alkoxy, $C_3$ to $C_{12}$ alkenyloxy and $C_2$ to $C_{12}$ alkenyl;
characterized in that said process comprises the step of forming the potassium salt of (I) by condensing a ketone of formula (II) with an ester of formula (III) in the presence of a potassium alcoholate (IV) (condensation step)

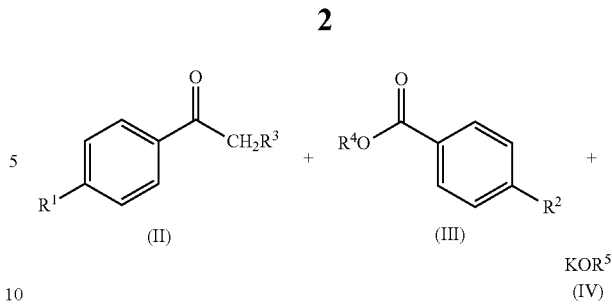

wherein
$R^1$ and $R^2$ are as defined above
$R^3$ is hydrogen;
$R^4$ is $C_1$ to $C_{12}$ alkyl and
$R^5$ is $C_1$ to $C_8$ alkyl.

In another embodiment, the invention relates to a process for the preparation of substituted dibenzoylmethane derivatives of formula (I) wherein $R^1$ and $R^2$ are independently selected from the group consisting of hydrogen, $C_1$ to $C_{12}$ alkyl, $C_1$ to $C_{12}$ alkoxy, $C_3$ to $C_{12}$ alkenyloxy and $C_2$ to $C_{12}$ alkenyl with the proviso that at least one of $R^1$ and $R^2$ is not hydrogen and with the proviso that the potassium alcoholate is derived from an alcohol $R^5$—OH having a boiling point below 100° C.

In a particular embodiment, the invention relates to a process for the preparation of dibenzoylmethane derivatives of formula (I) wherein $R^1$ and $R^2$ are independently selected from the group consisting of hydrogen, $C_1$ to $C_{12}$ alkyl and $C_1$ to $C_{12}$ alkoxy. More in particular $R^1$ is a $C_1$ to $C_8$ alkoxy radical and $R^2$ is a $C_1$ to $C_8$ alkyl radical, most in particular $R^1$ is a $C_1$ to $C_4$ alkoxy radical such as methoxy, ethoxy, isopropoxy, n-propoxy, 1-methylpropoxy, t-butoxy and n-butoxy and $R^2$ is a $C_1$ to $C_4$ alkyl radical such as methyl, ethyl, n-propyl, 1-methylethyl, n-butyl, 1-methylpropyl, 2-methylpropyl and 1,1-dimethylethyl. Most in particular, the invention relates to a process for the preparation of butyl methoxydibenzoylmethane (i.e. $R^1$ is methoxy and $R^2$ is 1,1-dimethylethyl).

Examples of alkyl, respectively alkenyl radicals are branched or unbranched alkyl, respectively alkenyl chains such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methyl pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, ethenyl, 2-propenyl and 3-butenyl.

Examples of alkoxy, respectively alkenyloxy radicals are e.g. methoxy, ethoxy, isopropoxy, n-propoxy, 1-methylpropoxy, n-butoxy, n-pentoxy, 2-methylpropoxy, 3-methylbutoxy, 1,1-dimethylpropoxy, 2,2-dimethylpropoxy, hexoxy, 1-methyl-1-ethylpropoxy, heptoxy, octoxy, 2-ethylhexoxy, 1,1-dimethylethoxy and allyloxy.

In the process according to the invention $R^4$ is advantageously a $C_1$ to $C_4$ alkyl radical such as methyl, ethyl, n-propyl, 1-methylethyl, n-butyl, 1-methylpropyl, 2-methylpropyl and 1,1-dimethylethyl. More advantageously, $R^4$ is methyl, ethyl or 1,1-dimethylethyl. Thus, in a specific embodiment, the invention relates to a process for the preparation of substituted dibenzoylmethane derivatives of formula (I) wherein $R^1$ is methoxy, $R^2$ is 1,1-dimethylethyl, and $R^4$ is methyl, ethyl or 1,1-dimethylethyl.

Suitable potassium alcoholates (IV) according to the invention encompass in particular potassium methylate, potassium tert.-butylate, potassium n-butylate, potassium-iso propylate, potassium tert.-amylate such as in particular potassium methylate or potassium tert.-butylate which are e.g. commercially available at Fluka or Suparna Chemicals. The potassium alcoholate may be used as such or it may be formed in situ e.g. by slow addition of a solution of the alcoholate in the respective alcohol into boiling toluene at continuous removal of the alcohol by distillation, thus forming a fine suspension/mixture of the potassium alcoholate in toluene which is subsequently used in the process according to the invention.

After the condensation step, the potassium salt of (I) is subsequently hydrolyzed to the respective substituted dibenzoylmethane derivative of formula (I) by known methods in the art, preferably by using a mineral or hydrocarbon acid such as sulphuric acid or acetic acid, in particular 5-85% sulphuric acid. The amount of acid can easily be adjusted by a person skilled in the art in order to achieve complete hydrolysis.

The process according to the present invention is advantageously carried out in an inert solvent. As known to a person skilled in the art, the term inert solvent refers to solvents which do not react chemically with the dissolved compounds. The solvent, which may be a pure substance or a mixture, is advantageously selected to have a high boiling point at atmospheric pressure so that the alcohol(s) released by the various reactions (from the alcoholate and the ester) may be removed without the removal of the solvent. Accordingly it is preferred that at atmospheric pressure the solvent has a boiling point of about 70° to 250° C., more preferably of about 80° to 150° C. Particular suitable solvents for the process according to the present invention are aromatic solvents such as alkyl or dialkyl benzenes or hydrocarbon solvents such a cyclohexane, methylcyclohexane, heptane or octane. Particularly advantageous solvents to be used in the process according to the present invention are toluene or xylene as well as mixtures thereof, in particular if $R^1$ is methoxy and $R^2$ is 1,1-dimethylethyl (thus the compound of formula (I) being butyl methoxydibenzoylmethane) as the potassium salt of butyl methoxydibenzoylmethane is particularly soluble in toluene or xylene which further facilitates the industrial handling.

Without being bound to theory, the structure of the intermediate potassium salt of butyl methoxydibenzoylmethane is believed to be as depicted below:

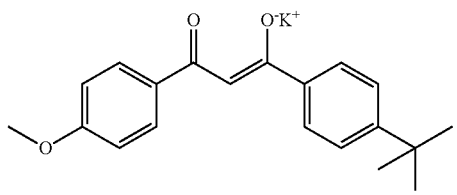

The reaction temperature is advantageously selected such that the in situ formed alcohols $R^4OH$ and $R^5OH$ are successively removed, preferably by distillation while refluxing the solvent. In all embodiment of the invention, the reaction temperature is preferably selected in the range of 70 C to 180° C. such as more preferably in the range of 80° C. to 150° C. and most preferably in the range of 80° 120° C.

Pressure is not critical to the present process, except to the extent that the selection of a particular pressure may lower the boiling point and may also facilitate removal of the alcohol(s) released in the reaction medium.

The ester of formula (III) is advantageously used in a slight excess in the process according to the present invention. In particular, the molar ratio of the ketone of formula (II) to the ester of formula (III) is selected in the range of about 0.5 to 1.25, such as more in particular in the range of 0.8 to 1, such as e.g. in the range of about 0.9 to 1. Generally, an excess of 1 to 10 mol-% of ester of formula (III) is used in relation to the ketone of formula (II).

The molar ratio of the ketone of formula (II) to the potassium alcoholate is advantageously less than 1. Particularly, the molar ratio is selected in the range of about 0.5 and 1.1, such as in the range of 0.8 to 1. Generally, an excess of about 0-30 mole-%, such as in particular of about 1-20 mole-% and more in particular of about 1-10 mol-% of potassium alcoholate is used based on the molar amount of the ketone of formula (II).

According to a preferred embodiment according to the invention a reaction mixture is provided that contains the potassium alcoholate, the ester of formula (III) and an inert solvent. To this mixture the ketone of formula (II) is added. The ketone of formula (II) can be added in pure form or in solution, alone or with a portion of the ester of formula (III) which is not in the starting mixture. In a preferred embodiment the alcohols are removed from the reaction mixture as they are formed.

Advantageously, the rate of addition of the ketone of formula (II) is selected such that the alcohol content in the reaction medium is kept low, preferably such that during the addition the alcohol is constantly being distilled off.

In a specific embodiment of the invention $R^1$ is methoxy, $R^2$ is 1,1-dimethylethyl, and $R^4$ is methyl, the solvent is toluene, the potassium base is potassium methylate or tert.-butylate and the reaction temperature is selected in the range of 80 to 120° C. at normal pressure. Even more in particular, the molar ratio of ketone of formula (II) to the ester of formula (III) is additionally selected in the range of 0.8 to 1 such as in particular in the range of about 0.9 to 1 and the molar ratio of the ketone of formula (II) to the potassium alcoholate is selected in the range of about 0.5 and 1.1 such as in the range of about 0.8 to 1.

Each reaction of the process according to the invention can in principle be carried out in any reactor suitable for the respective reaction type. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column.

In a further embodiment, when $R^1 \neq R^2$ (i.e. $R^1$ different from $R^2$), the invention also relates to substituted dibenzoylmethane derivatives of formula (I) obtained by the process according to the present invention as this process leads to a significant reduction of the respective symmetrical byproducts. Particularly, the invention relates to substituted dibenzoylmethane derivatives (I) obtained by the process according to the present invention, wherein the substituted dibenzoylmethane are chosen from the group consisting of

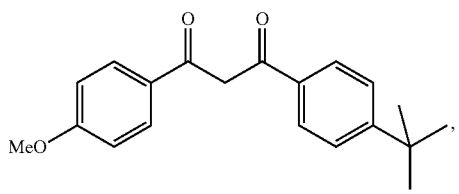

(V)

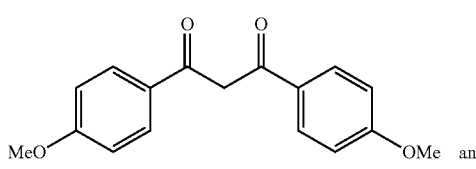

(VI) and

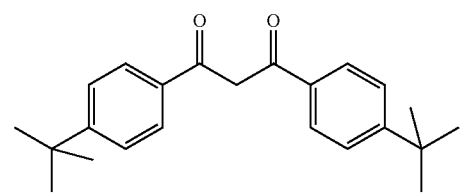

(VII)

More in particular, the invention relates to substituted dibenzoylmethane derivatives of formula (I) wherein the mol ratio of (V) (i.e. butyl methoxydibenzoylmethane) to the sum of (VI) (i.e. 4,4'-Dimethoxydibenzoylmethane) and (VII) (i.e. 4,4'-Di-tert-butyldibenzoylmethane) is in the range of 75:1 to 55 to 1.

In a further embodiment, the invention relates to a composition comprising a mixture of dibenzoylmethane derivatives of formula (V), (VI) and (VII) wherein the mol ratio of (V) to the sum of (VI) and (VII) is in the range of 75:1 to 55 to 1.

In one preferred embodiment, the composition consists of a mixture of dibenzoylmethane derivatives of formula (V), (VI) and (VII) wherein the mol ratio of (V) to the sum of (VI) and (VII) is in the range of 75:1 to 55 to 1

The term 'consisting of' as used according to the present invention means that the total amount of the compounds (V), (VI) and (VII) ideally sum up to 100 wt.-%. It is however not excluded that small amount of impurities or additives may be present such as e.g. in amounts of less than 5 wt.-%, preferably less than 3 wt.-%.

In another preferred embodiment, the composition comprising the substituted dibenzoylmethane derivatives of formula (V), (VI) and (VII) wherein the mol ratio of (V) to the sum of (VI) and (VII) is in the range of 75:1 to 55 to 1 is a topical composition furthermore comprising a topically acceptable carrier. Such compositions exhibit a decreased yellow discoloration. Preferably, the total amount of (V), (VI) and (VII) in such topical compositions is selected in the range of 0.1-10 wt.-% such as in the range of 0.5-5 wt.-% based on the weight of the topical composition.

The term "topical composition" as used herein refers in particular to cosmetic compositions that can be topically applied to mammalian keratinous tissue such as e.g. human skin or hair, particularly human skin.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic preparations as disclosed in A. Domsch, "Cosmetic Preparations", Verlag für chemische Industrie (ed. H. Ziolkowsky), 4$^{th}$ edition, 1992.

In a particular embodiment the topical compositions according to the invention are light-protective preparations (sun care products), such as sun protection milks, sun protection lotions, sun protection creams, sun protection oils, sun blocks or tropical's or day care creams with a SPF (sun protection factor). Of particular interest are sun protection creams, sun protection lotions, sun protection milks, sun spray preparations and sun protection preparations.

The following examples are provided to further illustrate the processes of the present invention. These examples are illustrative only and are not intended to limit the scope of the invention in any way.

EXAMPLE 1

4-tert-butyl-4'-methoxydibenzoylmethane: condensation with various bases

In a reaction flask with a 30 ml toluene and the base were provided under a blanket of inert gas. 20 mmole 4-tert-Butyl benzoic acid methyl ester (TBBM) and 20 mmole p-methoxy acetophenone (pMAc) was added. The mixture was stirred at about 110° C./1 bar while alcohol and toluene was slowly distilled off (toluene was occasionally replenished to maintain 20 ml volume). After complete conversion of TBBM and pMAc the reaction mixture was cooled and acidified with 2M acetic acid. An aliquot was analyzed by HPLC for the chemical yield of 4-tert-Butyl-4'-methoxy-dibenzoylmethane. The results are given in table 1.

TABLE 1

| | Results | | | |
|---|---|---|---|---|
| Base | Base [mmole] | Reaction [h] | Yield [mole %] | Appearance of reaction mixture |
| LiOMe | 30 | 22 | 18 | inhomogeneous |
| NaOMe | 22 | 6 | 74 | inhomogeneous |
| NaOtBu | 30 | 3 | 77 | inhomogeneous |
| Mg(OMe)$_2$ | 30 | 4 | 0 | inhomogeneous |
| NaH* | 22 | 2 | 81 | inhomogeneous |
| NaNH$_2$ | 22 | 2 | 64 | inhomogeneous |
| KOtBu | 22 | 2 | 87 | homogeneous |
| KOMe | 22 | 2 | 95 | homogeneous |
| KOC(CH$_3$)$_2$C$_2$H$_5$ | 22 | 2 | 95 | homogeneous |

*60% in mineral oil

As can be seen from the results in table 1 the use of a potassium alcoholate results in higher yields and shorter reaction times compared to the use of other alkali or earth alkali alcoholates.

Furthermore, the potassium salt did not crystallize and remained homogeneously dissolved in toluene whereas the sodium, magnesium and the lithium salt formed a crystalline inhomogeneous mixture.

EXAMPLE 2

4-tert-butyl-4'-methoxydibenzoylmethane: Influence of solvent/temperature

In a reaction flask with a stirrer-was provided at ambient temperature under a blanket of inert gas: 20 ml solvent, 22 mmole potassium tert.-butylate and 20.4 mmole tert.-butyl benzoic acid methyl ester. The mixture was heated to the reaction temperature given in table 2. Then, a 3 molar solution of p-methoxy acetophenone (pMAc) in the corresponding solvent was added over a period of about 1 h under slow distillation of a mixture of methanol, tert.-butanol and the respective solvent at the pressure given in table 2. Afterwards the homogeneous reaction mixture was stirred for additional 3 h during which the solvent was occasionally replenished to 20 ml volume. Then the reaction mixture was cooled and acidified with 2 m acetic acid. An aliquot was analyzed by HPLC giving the yields of 4-tert-butyl-4'-methoxydibenzoylmethane as indicated in table 2.

TABLE 2

| Solvent | Addition time pMAc [h] | T [° C.] | Time [h] | Pressure [bar] | Yield [mol %] |
|---|---|---|---|---|---|
| Xylene | 0.5 | 140° | 3 | 1 | 86 |
| Toluene | 0.5 | 110° | 3 | 1 | 91 |
| Toluene | 1.0 | 80° | 3 | 0.4 | 93 |

As can be retrieved from table 2, the reaction temperature is preferably kept in the range of 80-120° C.

EXAMPLE 3

4-tert-butyl-4'-methoxydibenzoylmethane

In a reaction flask with a stirrer was provided at ambient temperature under a blanket of inert gas: 16 ml toluene, 24 mmole base and 20.4 mmole 4-tert.butyl benzoic acid methylester (TBBM), respectively 20.4 mmole 4-tert.butyl benzoic acid tert.-butyl ester (TBBT) as indicated in table 3. The resulting reaction mixture was heated to boiling. Afterwards a 3 molar solution of p-methoxy acetophenone (pMAc) in toluene was added within 1 h under slow distillation of a mixture of methanol and/or tert.-butanol and toluene at 1 bar. The mixture was stirred for x additional hours as indicated in table 3. The reaction mixture was occasionally replenished to 20 ml volume by addition of toluene. The reaction mixture was cooled and acidified with 2M acetic acid. An aliquot was analyzed by HPLC for the chemical yield of 4-tert-butyl-4'-methoxydibenzoylmethane. The results are presented in table 3.

TABLE 3

| Base | Ester | Appearance of reaction mixture | time [h] | Yield [mole %] |
|---|---|---|---|---|
| KOMe | TBBT | homogeneous | 1.75 | 91 |
| KOtBu | TBBT | homogeneous | 2 | 85 |
| KOtBu | TBBM | homogeneous | 3 | 92 |
| NaOtBu | TBBT | inhomogeneous | 1.75 | 63 |
| NaOMe | TBBT | inhomogeneous | 4 | 80 |
| NaOtBu | TBBM | inhomogeneous | 3 | 85 |

TBBT = 4-(1,1-dimethylethyl)-benzoic acid tent-butyl ester
TBBM = 4-(1,1-dimethylethyl)-benzoic acid methyl ester As can be retrieved from table 3 highest yields of butyl methoxydibenzoylmethane were achieved with either the tert-butylester TBBT and potassium methylate or the methylester TBBM with potassium tert-butylate, whereas the combination of the tert-butylester TBBT with potassium tert-butylate resulted in lower yields.

Furthermore, as can be retrieved from table 3, the use of the respective sodium alcoholate resulted in significant lower yields compared to the use of the respective potassium alcoholate. Furthermore, the use of sodium alcoholate resulted in inhomogeneous badly stirrable reaction mixtures.

EXAMPLE 4

4-tert-butyl-4'-methoxydibenzoylmethane

In a reaction flask with a stirrer-was provided under a blanket of nitrogen a solution of 20.21 g 4-t-butylbenzoic acid methylester 98% (103 mmole) in 100 ml toluene. To the solution was added 8.57 g potassium methoxide solid >90% Fluka (110 mmole) and the mixture was heated to boiling. To the boiling mixture was added in 1 h at continuous distillation of the formed methanol a solution of 15.32 g p-methoxyacetophenone Fluka 98% (100 mmole) in 20 g toluene. The clear brownish reaction solution was stirred for additional 2 h and slow distillation. The mixture was cooled and acidified by addition of 115 ml 0.5 mol/l sulfuric acid. The water-phase was separated followed by extraction in a funnel with 100 ml toluene. The organic phases where washed with water, combined and the toluene evaporated at a rotavapor resulting in 30.81 g of a residue. The respective yields of 4-tert-butyl-4'-methoxydibenzoylmethane (BM-DBM) 4,4'-dimethoxydibenzoylmethane (DMDBM) and 4,4'-di-tert-butyldibenzoylmethane (DTBDBM) are given in table 5.

The experiment was repeated with different bases resulting in the yields as indicated in table 5 as well.

TABLE 5

| Toluene [ml] | Base [g] | Yield [mol-%] | | | Mol ratio |
|---|---|---|---|---|---|
| | | BMDBM | DMDBM | DTBDBM | BMDBM/Σ DMDBM&DTBDBM |
| 160 | NaOMe: 6.48 | 80 | 1.9 | 0.9 | 29:1 |
| 100 | KOtBu: 12.34 | 93 | 1.1 | 0.5 | 58:1 |
| 100 | KOMe: 8.57 | 90 | 0.8 | 0.5 | 69:1 |

As can be retrieved from table 5, the yields of 4-tert-butyl-4'-methoxydibenzoylmethane are significantly higher when a potassium alcoholate is used. Furthermore the amount of the symmetrical by-products 4,4'-dimethoxydibenzoylmethane and 4,4'-di-tert.-butyldibenzoylmethane is significantly reduced which results in a decreased yellow discoloration after incorporation into a topical composition.

EXAMPLE 5

4-Allyloxy-4'-tert.butyl-dibenzoylmethane

To a mixture of 2.9 g 4-tert-butylbenzoic acid methylester (15 mmole), 1.25 g potassium methoxide (18 mmole) in 10 ml toluene was added a solution of 2.47 g 4-allyloxy acetophenone (14 mmole) in 5 ml toluene. The mixture was boiled for 1 h at 105° C.-110° C. resulting in a homogeneous mixture. The solution was acidified at ambient temperature with diluted sulfuric acid, extracted with toluene and washed with water. The extract was evaporated and the residue crystallized from methanol yielding 3.39 g (72%) of 4-tert-.butyl-4'allyloxy-dibenzoylmethane.

EXAMPLE 6

4,4'-Dimethoxy-dibenzoylmethane

To a mixture of 1.67 g 4-methoxy benzoic acid methylester (10 mmole) and 0.86 g potassium methoxide (12 mmole) in 10 ml toluene was added a solution of 1.52 g 4-methoxyacetophenone (10 mmole) in 5 ml toluene. The mixture was boiled for 2 h at 105° C.-110° C. resulting in a homogeneous mixture. The mixture was acidified with diluted hydrochloric acid, extracted with toluene and washed with water. The extract was evaporated and the residue crystallized from ethyl acetate yielding 2.02 g (71%) 4,4'-dimethoxy-dibenzoylmethane

EXAMPLE 7

4-tert-butyl-4'-methoxydibenzoylmethane: variability of solvent

To a mixture of 20 ml solvent, 26 mmole potassium methylate (Fluka) and 4.04 g 4-tert.-butyl benzoic acid methylester (21 mmole) was added 3.00 g 4-methoxyacetophenone (20 mmole) and 6 ml solvent as indicated in table 6 at boiling temperature and distillation of solvent. The mixture was boiled for additional 2 h and continued distillation (the solvent was replenished on occasion to maintain at least 20 ml volume). The mixture was cooled to ambient temperature and acidified with 2M acetic acid. An aliquot was analyzed by HPLC to determine the chemical yield of 4-tert-butyl-4'-methoxydibenzoylmethane.

TABLE 6

| No | Solvent | Yield [mole %] |
|---|---|---|
| 1 | Chlorobenzene | 85 |
| 2 | Benzene | 90 |
| 3 | 1,2-Diethoxyethane | 83 |
| 4 | Octane | 82 |

The invention claimed is:
1. A process for the preparation of substituted dibenzoylmethane derivatives of formula (I):

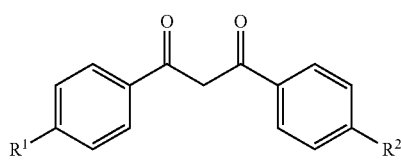

(I)

wherein R1 and R2 are independently selected from the group consisting of hydrogen, $C_1$ to $C_{12}$ alkyl, $C_1$ to C12 alkoxy, $C_3$ to $C_{12}$ alkenyloxy and C2 to $C_{12}$ alkenyl; and wherein
the process comprises the step of forming the potassium salt of formula (I) with a yield of 85% or greater by condensing in a condensation step a homogenous reaction mixture of a ketone of formula (II) with an ester of formula (III) in the presence of a potassium alcoholate of formula (IV):

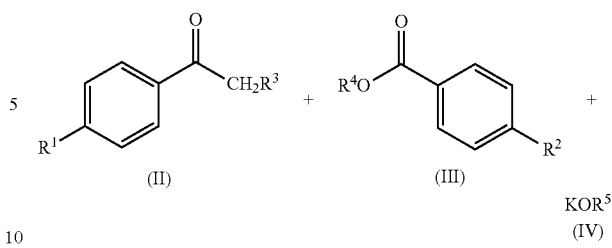

wherein $R^1$ and $R^2$ are as defined above; $R^3$ is hydrogen; $R^4$ is $C_1$ to $C_{12}$ alkyl and $R^5$ is $C_1$ to $C_8$ alkyl;
with the proviso that at least one of $R^1$ and $R^2$ is not hydrogen and with the proviso that the potassium alkoxide is of an alcohol $R^5$—OH having a boiling point below 100° C.

2. The process according to claim 1 wherein $R^1$ and R2 are independently selected from the group consisting of hydrogen, C1 to $C_{12}$ alkyl and C1 to C12 alkoxy.

3. The process according to claim 1 wherein $R^3$ is hydrogen and $R^4$ is methyl, ethyl or 1,1 dimethylethyl.

4. The process according to claim 1 wherein the condensation step is carried out in an inert solvent.

5. The process according to claim 4 wherein the inert solvent is toluene and/or xylene, preferably toluene.

6. The process according to claim 1 wherein the potassium alcoholate is at least one selected from the group consisting of potassium methylate and potassium tert-butylate.

7. The process according to claim 1 wherein the process comprises continuously removing the alcohols $R^4OH$ and $R^5OH$ as the alcohols are formed.

8. The process according to claim 1 wherein $R^1$ is methoxy, $R^2$ is 1,1 dimethylethyl and $R^4$ is methyl, ethyl or 1,1 dimethylethyl.

9. The process according to claim 1 wherein the molar ratio of the ketone of formula (II) to the ester of formula (III) is in a range of 0.5 to 1.25.

10. The process according to claim 1 wherein the molar ratio of the ketone of formula (II) to the potassium alcoholate is in a range of 0.5 to 1.1.

11. The process according to claim 1, wherein the solvent is toluene, and wherein the process is conducted at a reaction temperature which is in a range of 80° to 120° C.

12. The process according to claim 1, wherein following the condensation step the process comprises a step of hydrolysis using an organic or mineral acid.

13. The process according to claim 12 wherein the mineral acid is sulfuric acid.

14. A composition comprising substituted dibenzoylmethane derivatives of formula (V), formula (VI) and formula (VII):

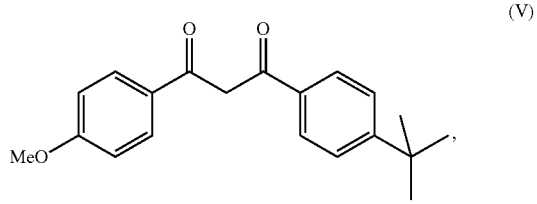

(V)

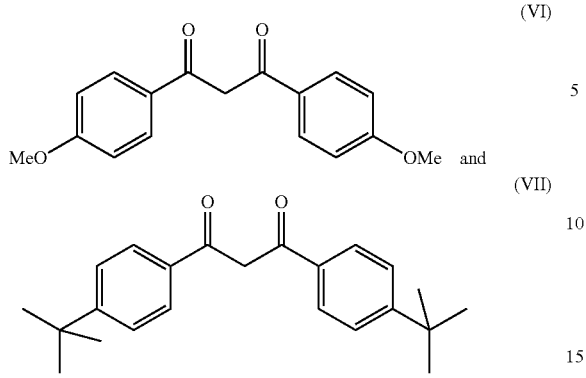

wherein the molar ratio of formula (V) to the sum of formula (VI) and formula (VII) is in a range of 75:1 to 55:1.

15. A topical composition comprising the composition according to claim 14, and a topical carrier.

16. The process according to claim 6, wherein the potassium alcoholate is potassium methylate.

17. The process according to claim 9, wherein the molar ratio of the ketone of formula (II) to the ester of formula (III) is in a range of 0.9 to 1.

18. The process according to claim 10, wherein the molar ratio of the ketone of formula (II) to the potassium alcoholate is in a range of 0.8 to 1.

19. The process according to claim 12 wherein the hydrolysis is conducted using a mineral acid.

* * * * *